United States Patent [19]

Buerstinghaus et al.

[11] Patent Number: 4,710,494

[45] Date of Patent: Dec. 1, 1987

[54] BISTHIOPHOSPHATES AND THEIR USE FOR CONTROLLING PESTS

[76] Inventors: Rainer Buerstinghaus, Heidelberg; Heinrich Adolphi, Limburgerhof, both of Fed. Rep. of Germany

[21] Appl. No.: 867,574

[22] Filed: May 28, 1986

[30] Foreign Application Priority Data

Jun. 5, 1985 [DE] Fed. Rep. of Germany ....... 3520112
Jun. 28, 1985 [DE] Fed. Rep. of Germany ....... 3523183

[51] Int. Cl.$^4$ .............................................. A01N 57/02
[52] U.S. Cl. ..................................... 514/143; 558/208
[58] Field of Search .......................... 558/208; 514/143

[56] References Cited

U.S. PATENT DOCUMENTS 3,518,261  6/1970  Nguyen et al. ...................... 558/208
3,725,546  4/1973  Tsuchiya et al. ................... 558/208
3,933,947  1/1976  Kishino et al. ..................... 558/208

FOREIGN PATENT DOCUMENTS 0042508 12/1981 European Pat. Off. .

*Primary Examiner*—Anton H. Sutto
*Attorney, Agent, or Firm*—Keil & Weinkauf

[57] ABSTRACT

Benzylbisthiophosphates of the formula

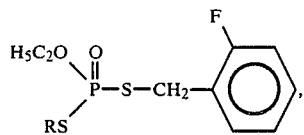

where R is straight-chain or branched alkyl of 3 to 5 carbon atoms, their manufacture, and their use as pesticides.

7 Claims, No Drawings

BISTHIOPHOSPHATES AND THEIR USE FOR CONTROLLING PESTS

The present invention relates to novel bisthiophosphates, a process for their preparation, pesticides which contain these bisthiophosphates as active ingredients, and a method of controlling pests with these active ingredients.

Active ingredients from the group consisting of the benzylbisthiophosphates which are useful for controlling pests are disclosed in German Laid-Open Application DOS No. 2,111,589 and European Patent Publication No. 81 104 212.6. They can be used as insecticides, acaricides and nematicides, but their action is not always completely satisfactory, especially with low concentrations.

We have found that benzylbisthiophosphates of the formula I

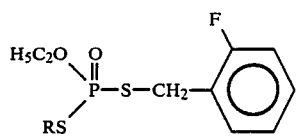

where R is straight-chain or branched alkyl of 3 to 5 carbon atoms, control pests from the class consisting of the insects and nematodes more effectively than known bisthiophosphates.

Examples of alkyl radicals R are n-propyl, isopropyl, isobutyl, sec-butyl and 3-methylbutyl.

The novel compounds are prepared by reacting a known or commercially available benzyl halide of the formula II

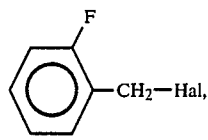

where Hal is halogen, with a salt of a dithiophosphoric acid derivative of the formula III

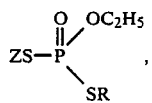

where R has the meaning stated in claim 1 and Z is an alkali metal ion, one eqivalent of an alkaline earth metal ion or an unsubstituted or alkyl-substituted ammonium ion.

Particularly suitable halogen atoms in formula II are chlorine and bromine. In formula III, Z is preferably a sodium or potassium ion or an ammonium or methylated ammonium ion. The dimethylammonium ion is particularly useful for the reaction.

The reaction is carried out in a manner conventionally used for reacting organic halogen compounds with alkali metal salts, and is effected, for example, at below 150° C. in a solvent or diluent. Examples of suitable substances for this purpose are water, alcohols, such as methanol, ethanol or propanol, ethers, such as tetrahydrofuran, dioxane or diglycol dimethyl ether, ketones such as acetone, methyl ethyl ketone or diethyl ketone, aromatic hydrocarbons, such as toluene, xylene or chlorobenzene; nitriles, such as acetonitrile or propionitrile, and polar aprotic solvents, such as dimethylformamide or dimethyl sulfoxide. Mixtures of these solvents and diluents may also be used. Where nonaqueous solvents are used, it may be advantageous to add a catalytic amount of potassium iodide to increase the reactivity.

The starting materials may be used in, or with an excess of, one or other of the reactants.

The novel active ingredient is obtained from the reaction mixture in a conventional manner, for example by the addition of water, separation of the phases and distillation and/or column chromatography.

Some of the novel compounds of the formula I are obtained in the form of colorless or slightly brownish oils, which can be freed from the final volatile constituents by prolonged heating to moderately elevated temperatures under reduced pressure (incipient distillation), and purified in this manner.

The Example which follows illustrates the preparation of the compounds according to the invention.

PREPARATION EXAMPLE 1

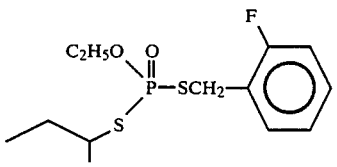

A solution of 18.65 g of dimethylammonium O-ethyl-S-sec-butyldithiophosphate and 8.66 g of 2-fluorobenzyl chloride in 60 ml of acetonitrile is heated for 7 hours at 65° C. The solution is cooled, the solvent is stripped off in a rotary evaporator, the residue is taken up in ether and the solution is then washed thoroughly with water. The organic phase is dried over sodium sulfate, the solvent is removed under reduced pressure and the residue is subjected to incipient distillation under 0.01 mbar and at 50° C. 15.3 g of O-ethyl S-sec-butyl S-(2-fluorobenzyl)dithiophosphate are obtained in the form of a straw-colored oil. Yield: 79% of theory.

|  | $C_{13}H_{20}FO_2PS_2$ (322) | |
|---|---|---|
| Calculated: | C 48.4 | H 6.3 |
| Found: | C 48.5 | H 6.3 |

Infrared absorptions in the fingerprint region (cm$^{-1}$): 1457, 1234, 1096, 1016, 953.

Where they are identified by infrared absorptions, the compounds listed as Examples 2-6 in the Table below were likewise obtained in the manner described in Example 1; other compounds of the formula (I) can be obtained in the same way, with appropriate modification of the method in respect of the particular amount required and after a preliminary experiment to determine the best reaction conditions.

TABLE

| Example No. | R | Infrared absorptions (cm$^{-1}$) |
|---|---|---|
| 2 | isopropyl | 1380, 1360, 1230, 1015, 950 |
| 3 | n-propyl | 1290, 1230, 1090, 1015, 950 |
| 4 | isobutyl | 1380, 1360, 1250, 1090, 1015 |
| 5 | 3-methylbutyl | 1380, 1360, 1230, 1090, 1015 |

TABLE-continued

| Example No. | R | Infrared absorptions (cm$^{-1}$) |
|---|---|---|
| 6 | tert-butyl | |

The above, and other, active ingredients according to the invention are employed in the manner usual for phosphoric acid esters. Details on formulation, application techniques and mode of action, and details of suitable mixture components for achieving synergistic and other advantageous actions are given for example in U.S. Pat. No. 4,320,122, which is incorporated herein by reference.

The following active ingredients were used in the examples below for comparison purposes:

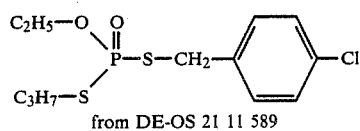

from DE-OS 21 11 589  I

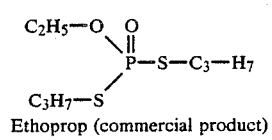

Ethoprop (commercial product)  II

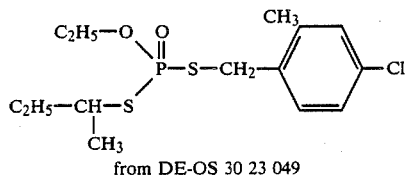

from DE-OS 30 23 049  III

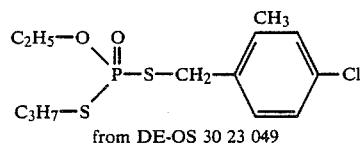

from DE-OS 30 23 049  IV

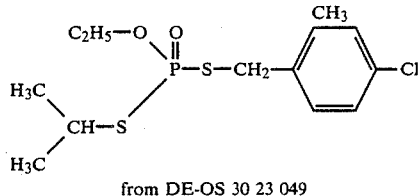

from DE-OS 30 23 049  V

Contact action on oriental cockroaches (*Blatta orientalis*)

The bottoms of 1 liter preserving jars were treated with acetonic solutions of the active ingredients.

After the solvent had evaporated, 5 adult cockroaches were placed in each jar.

The kill rate was determined after 48 hours.

| | mg | Percentage kill |
|---|---|---|
| Compound 1 | 0.08 | 100 |
| Compound 3 | 0.1 | 100 |
| Compound 4 | 0.1 | 100 |
| Comparative agent I | 0.2 | 100 |
| Comparative agent III | 0.25 | 100 |
| Comparative agent IV | 0.5 | 100 |

| | mg | Percentage kill |
|---|---|---|
| Comparative agent V | 1.0 | 80 |

Continuous contact action on houseflies (*Musca domestica*)

The insides of Petri dishes 10 cm in diameter were lined with acetonic solutions of the active ingredients.

After the solvent had evaporated, 20 4-day old houseflies were introduced into each dish.

The kill rate was determined after 4 hours.

| | mg | Percentage kill |
|---|---|---|
| Compound 1 | 0.02 | 100 |
| Compound 3 | 0.02 | 100 |
| Comparative agent I | 0.2 | 100 |
| Comparative agent III | 0.2 | 80 |
| Comparative agent IV | 2.0 | 100 |
| Comparative agent V | 2.0 | 100 |

Contact action on granary weevils (*Sitophilus granarius*)

Petri dishes 10 cm in diameter were lined with acetonic solutions of the active ingredients. After the solvent had evaporated, 100 weevils were placed in each dish. After 4 hours the weevils were transferred to untreated vessels. The kill rate was determined after 24 hours by ascertaining how many weevils were able, after this period, to leave an untreated cardboard dish (40 mm in diameter, 10 mm high) within 60 minutes.

| | mg | Percentage kill |
|---|---|---|
| Compound 1 | 0.02 | 100 |
| Compound 1 | 0.01 | approx. 80 |
| Compound 3 | 0.04 | approx. 80 |
| Compound 4 | 0.02 | 100 |
| Comparative agent I | 0.1 | 100 |
| Comparative agent II | 0.1 | 100 |
| Comparative agent III | 0.1 | approx. 80 |
| Comparative agent IV | 1.0 | 100 |
| Comparative agent V | 1.0 | 80 |

Breeding experiment with houseflies (*Musca domestica*)

4.5 ml of skimmed milk was introduced into 50 ml penicillin flasks, and 0.5 ml of the aqueous active ingredient formulation was then added. After brief mixing, a ball of absorbent cotton was introduced and about 50 housefly larvae placed on it. The flasks were covered and kept at room temperature. The development was assessed after 7 days.

| | mg | Percentage kill |
|---|---|---|
| Compound 1 | 0.05 | 100 |
| Comparative agent I | 5.0 | 100 |
| Comparative agent II | 2.5 | 100 |
| Comparative agent IV | 10 | approx. 80 |
| Comparative agent V | 50 | 80 |

Contact action and effect of ingested food on caterpillars of the diamondback moth (*Plutella maculipennis*)

Leaves of young cabbage plants were dipped for 3 seconds in aqueous emulsions of the active ingredients and, after excess liquid had been briefly allowed to drip off, were placed on a moist filter paper in a Petri dish. 10 caterpillars of the 4th stage were then put on each leaf. The action was assessed after 48 hours.

|  | Percentage concentration | Percentage kill |
|---|---|---|
| Compound 1 | 0.005 | 100 |
| Compound 2 | 0.05 | 100 |
| Compound 3 | 0.02 | 100 |
| Compound 4 | 0.01 | 100 |

Contact action on ticks (*Ornithodorus moubata*)

The experiment was carried out on young ticks which had sucked blood only once. Commercially available tea-bags, each containing 5 animals, were dipped for 5 seconds in the aqueous active ingredient formulation. The bags were then suspended. The temperature was kept at 25° to 26° C. The kill rate was determined after 48 hours.

|  | Percentage concentration | Percentage kill |
|---|---|---|
| Compound 1 | 0.0025 | 80 |
| Compound 4 | 0.0025 | 100 |
| Comparative agent III | 0.04 | 100 |

Action on root-knot nematodes (*Meloidogyne incognita*)

30 ml of aqueous formulations of the active ingredients was intimately mixed with 300 g of mold heavily infested with *Meloidogyne incognita*. The mold was then filled into plastic pots and tomato seedlings were planted therein. The pots were kept under greenhouse conditions at from 22° to 24° C.

The roots were investigated as to root-knot formation after 6 to 8 weeks.

|  | Percentage concentration |  |
|---|---|---|
| Compound 1 | 0.02 | 100% kill |
| Compound 1 | 0.01 | approx. 80% inhibition |
| Comparative agent III | 0.05 | approx. 80% inhibition |
| Comparative agent IV | 0.05 | approx. 80% inhibition |
| Comparative agent V | 0.1 | no inhibition |

We claim:

1. A benzylbisthiophosphate of the formula

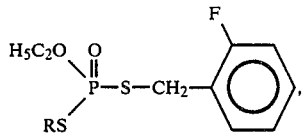

where R is straight-chain or branched alkyl of 3 to 5 carbon atoms.

2. A compound as described in claim 1, wherein R is sec. butyl.

3. A compound as described in claim 1, wherein R is isopropyl.

4. A compound as described in claim 1, wherein R is isobutyl.

5. A compound as described in claim 1, wherein R is 3-methylbutyl.

6. A process for combatting pests, wherein an effective amount of a compound of the formula I as set forth in claim 1 is allowed to act on the pests or their habitat.

7. A pesticide containing a solid or liquid carrier and an effective amount of at least one compound of the formula I as set forth in claim 1.

* * * * *